(12) United States Patent
Keränen et al.

(10) Patent No.: US 10,195,021 B2
(45) Date of Patent: Feb. 5, 2019

(54) MEDICAL DEVICE FOR A CARDIAC VALVE IMPLANT

(75) Inventors: Olli Keränen, Bjärred (SE); Jani Virtanen, Helsinki (FI)

(73) Assignee: Medtentia International Ltd. Oy, Helsinki (FI)

(*) Notice: Subject to any disclaimer, the term of this patent is extended or adjusted under 35 U.S.C. 154(b) by 0 days.

(21) Appl. No.: 14/111,509

(22) PCT Filed: May 4, 2012

(86) PCT No.: PCT/EP2012/058278
§ 371 (c)(1),
(2), (4) Date: Dec. 4, 2013

(87) PCT Pub. No.: WO2012/150346
PCT Pub. Date: Nov. 8, 2012

(65) Prior Publication Data
US 2014/0081394 A1    Mar. 20, 2014

Related U.S. Application Data

(60) Provisional application No. 61/482,231, filed on May 4, 2011.

(30) Foreign Application Priority Data

May 4, 2011 (EP) ..................... 11164750

(51) Int. Cl.
*A61F 2/24* (2006.01)
*A61B 17/28* (2006.01)

(52) U.S. Cl.
CPC .......... *A61F 2/2409* (2013.01); *A61F 2/2445* (2013.01); *A61F 2/2466* (2013.01);
(Continued)

(58) Field of Classification Search
CPC .................. A61F 2/2427; A61F 2/2466; A61F 2250/0097; A61F 2/2445; A61F 2/2409; A61F 2230/0091
See application file for complete search history.

(56) References Cited

U.S. PATENT DOCUMENTS 3,469,494 A * 9/1969 Frailly ..................... 411/517
6,458,867 B1 * 10/2002 Wang et al. ............... 523/105
(Continued)

FOREIGN PATENT DOCUMENTS

WO   WO2001/050985 A1   7/2001
WO   WO2004/071333 A2   8/2004
(Continued)

OTHER PUBLICATIONS

WIPO, European International Preliminary Examining Authority, International Preliminary Report on Patentability dated Sep. 24, 2013 in International Patent Application No. PCT/EP2012/058278, 10 pages.
(Continued)

*Primary Examiner* — Dinah Baria
(74) *Attorney, Agent, or Firm* — Inskeep IP Group, Inc.

(57) ABSTRACT

A medical device for holding a cardiac valve implant includes an elongate support defining a peripheral edge with a curvature about which the cardiac valve implant can be fitted. The elongate support includes a resilient portion for resiliently holding the cardiac valve implant in place in the device, and a support tool for holding a cardiac valve implant comprising first and second elongate support members being separate and radially movable in relation to each other, each having a curvature about which the cardiac valve implant can be fitted and a manipulator portion connected to the first and second elongate support members.

11 Claims, 11 Drawing Sheets

(52) U.S. Cl.
CPC ..... *A61B 17/282* (2013.01); *A61F 2230/0091* (2013.01); *A61F 2250/0097* (2013.01)

(56) References Cited

U.S. PATENT DOCUMENTS

| | | |
|---|---|---|
| 2003/0176916 A1 | 9/2003 | Ryan et al. |
| 2005/0043791 A1* | 2/2005 | McCarthy et al. .......... 623/2.36 |
| 2006/0176916 A1 | 8/2006 | Zanger et al. |
| 2006/0282162 A1 | 12/2006 | Nguyen et al. |

FOREIGN PATENT DOCUMENTS

| | | |
|---|---|---|
| WO | WO2005/112832 A1 | 12/2005 |
| WO | WO2005/122964 A1 | 12/2005 |

OTHER PUBLICATIONS

WIPO, European International Search Authority, International Search Report and Written Opinion dated Sep. 10, 2012 in International Patent Application No. PCT/EP2012/058278, 16 pages.

* cited by examiner

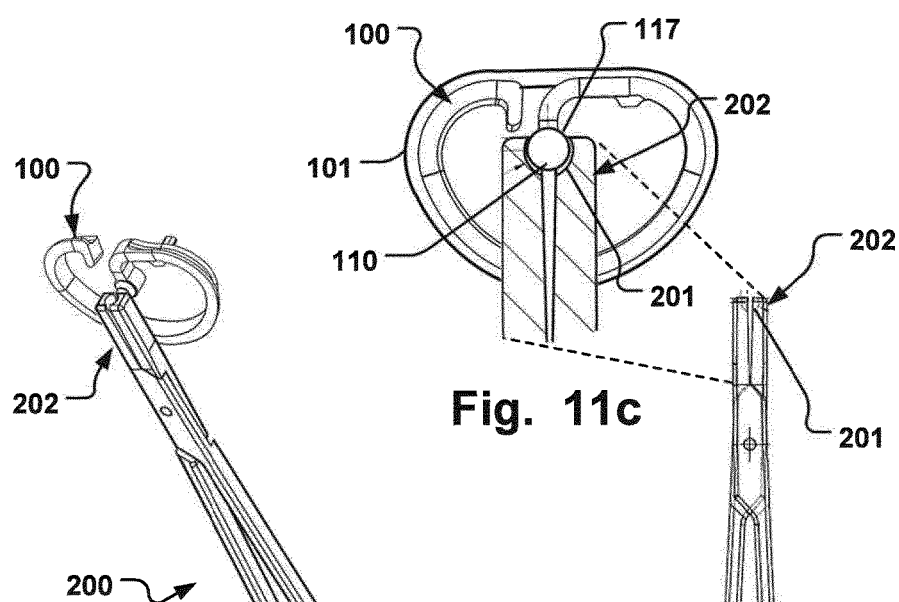
Fig. 11c
Fig. 11a
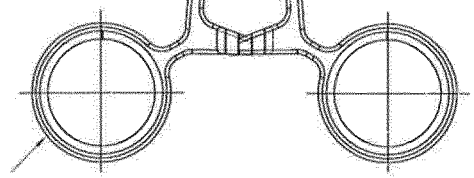
Fig. 11b

MEDICAL DEVICE FOR A CARDIAC VALVE IMPLANT

RELATED APPLICATIONS

This application is the U.S. National Phase of and claims priority to International Patent Application No. PCT/EP2012/058278, International Filing Date May 4, 2012, entitled Medical Device For A Cardiac Valve Implant, which claims benefit of U.S. Provisional Application Ser. No. 61/482,231, filed May 4, 2011 entitled Medical Device For A Cardiac Valve Implant, and European Application No. EP11164750.9, filed May 4, 2011 entitled Medical Device For A Cardiac Valve Implant; all of which are incorporated herein by reference in their entireties.

FIELD OF THE INVENTION

This invention pertains in general to the field of cardiac valve replacement and repair. More particularly the invention relates to a medical device for holding a cardiac valve implant, a method of holding a cardiac valve implant, a kit comprising a tool for manipulation of such medical device, and a support tool for holding a cardiac valve implant.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. Such annuloplasty rings or other annuloplasty implants or cardiac valve implants in general such as replacement valves, are put into position by various tools.

An assembly for holding an annuloplasty ring in place for placing a suture line and attach the ring to the annulus tissue is disclosed in U.S. Pat. No. 6,197,052. The annuloplasty ring or suture guide is releasably attached to a guide mount by sutures or threads passing through apertures disposed in the guide mount and through the ring. Once the surgeon is ready to release the ring, the sutures for fixing the ring to the mount are cut of at various locations of the mount, and the guide can subsequently be retrieved. The mount is attachable to a handle assembly which is mounted by inserting a cylindrical hub of the handle assembly into a plug of the mount.

United states patent application US2003176916 discloses a holder for an annuloplasty prosthesis having a first component, around which the prosthesis is mounted and a second component, releasably secured to the first component by sutures. Projections align the two holder components to each other, and a further rectangular projection at the second component is required to prevent deformation and reduction of the circumference of the first holder component which is an open ring. I.e. the first holder component can not satisfactory hold the prosthesis without the second holder component. In some embodiments, rather than retaining the prosthesis to the holder by means of sutures passing through the prosthesis, the prosthesis is retained by means of downwardly extending penetrating members such as barbs, pins, pegs, or needles.

Hence, a problem with prior art devices is the risk of damaging the implant due to complicated mechanisms for attachment and detachment to the holder, thereby increasing the amount of manipulation of the implant both during the positioning phase and during repositioning, which may lead to unnecessary wear and risk of damages to the implant.

During heart surgery, a premium is placed on reducing the amount of time used to replace and repair valves as the heart is frequently arrested and without perfusion. A problem with prior art devices is the time consuming attachment or detachment of the annuloplasty device, also referred to as the cardiac valve implant, or simply implant below, to the holder assembly, e.g. by using sutures. It would therefore be very useful to have a medical device for holding the implant to be positioned at the annulus that can be quickly attached or detached to such implant.

If repositioning of the cardiac valve implant becomes necessary it is also critical that the holder can engage the implant easily and quickly. The suture attachment in prior art devices is complicated and time consuming when such repositioning is required.

Another problem with prior art devices is insufficient visibility through the holder and into the annulus due to complex holder construction with elements extending across the annulus and thereby obscuring the sight. Reduced visibility makes accurate positioning more complicated and time consuming with potentially increased risk.

A further problem with prior art devices is insufficient maneuverability of the cardiac valve implant due to lack of freedom of movement between the holder and the delivery tool. Such lack of flexibility also increases the time of the replacement or repair procedure.

Another problem with prior art holders is the limited ability to adapt to implants having a wide range of sizes. It is therefore necessary to have a number of various holders which complicates the procedure further as frequent exchange of holders may be necessary to find the correct fit.

The above problems may have dire consequences for the patient and the health care system. Patient risk is increased.

Hence, an improved medical device for holding a cardiac valve implant would be advantageous and in particular allowing for increased flexibility, reducing the time of lengthy surgery procedures, cost-effectiveness, and increased patient safety. Also, a method of holding a cardiac valve implant with such medical device and a kit comprising a tool for manipulation of such medical device would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device according to the appended patent claims.

According to a first aspect of the invention a medical device for holding a cardiac valve implant is provided comprising an elongate support defining a peripheral edge with a curvature about which the cardiac valve implant can be fitted, wherein the elongate support comprises a resilient portion for resiliently holding the cardiac valve implant in place in said device.

According to a second aspect of the invention a kit is provided comprising a medical device according to the first aspect having a resilient portion, and a tool comprising a distal end arranged for manipulation of the resilient portion for resiliently holding a cardiac valve implant in place in the device.

According to a third aspect of the invention a method of holding a cardiac valve implant in place by a medical device according to the first aspect external of a patient body is provided, comprising providing a kit according to the second aspect, and resiliently holding the cardiac valve implant in place in the device.

According to a fourth aspect of the invention a support tool for holding a cardiac valve implant is provided comprising first and second elongate support members being separate and radially movable in relation to each other, and each having a curvature about which the cardiac valve implant can be fitted, a manipulator portion connected to the first and second elongate support members for moving at least one of the first and second elongate support members in relation to each other to cause the curvature to conform at least partly to the cardiac valve implant to hold the cardiac valve implant in place.

According to a fifth aspect of the invention a method of holding a cardiac valve implant in place by a medical device according to the fourth aspect external of a patient body is provided, comprising fixing the position of said implant to said device by moving at least one of the first and second elongate support members in radially opposite directions by manipulator portions of said device to cause the curvature of said support members to conform at least partly to the cardiac valve implant to hold the cardiac valve implant in place.

Further embodiments of the invention are defined in the dependent claims, wherein features for the second and subsequent aspects of the invention are as for the first aspect mutatis mutandis.

Some embodiments of the invention provide for less time consuming positioning of cardiac valve implants at a target site in the heart.

Some embodiments of the invention provide for less time consuming attachment and detachment of a cardiac valve implant to a medical device for efficient positioning and repositioning of such implant at the annulus.

Some embodiments of the invention provide for flexible positioning of a cardiac valve implant at a target site by conforming to varying anatomical sites in a body.

Some embodiments of the invention provide for increased visibility through the cardiac valve implant and into the annulus for accurate positioning and reducing the risk of complications.

Some embodiments of the invention also provide for a reduced risk of damaging the cardiac valve implant during a repair or replacement procedure.

Some embodiments of the invention provide for a compact holder of a cardiac valve implant with maintained flexibility of positioning.

Some embodiments of the invention provide for a flexible holder in terms of adapting to a wide range of sizes of cardiac valve implants to be positioned.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 11a-c are illustrations of a tool for holding a medical device according to embodiments of the invention.

DESCRIPTION OF EMBODIMENTS

Figure 1A:
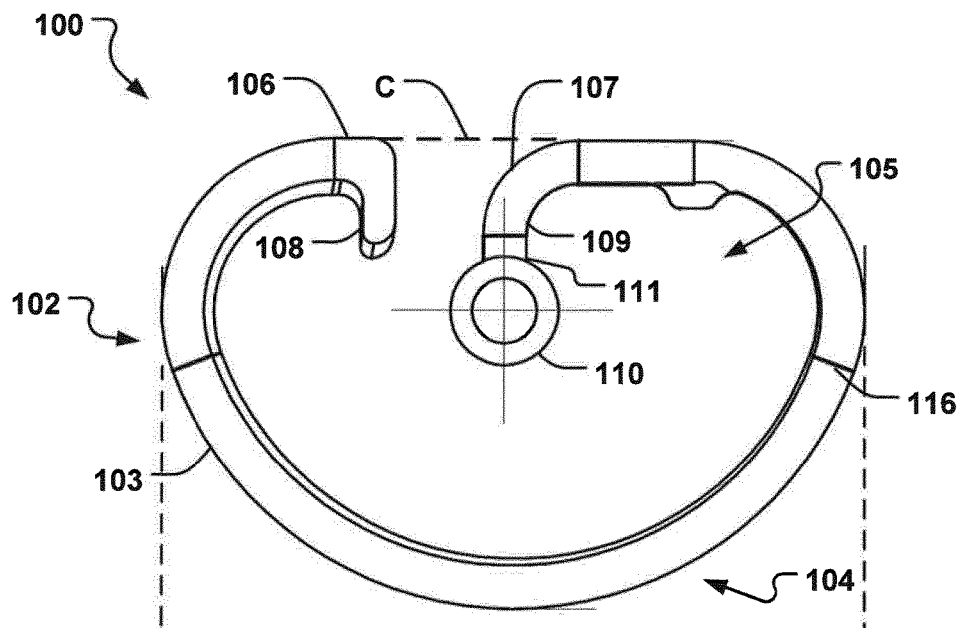
FIGS. 1a-b are illustrations of a medical device according to an embodiment of the invention in a first configuration (a) and in a second configuration (b)

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 1B:
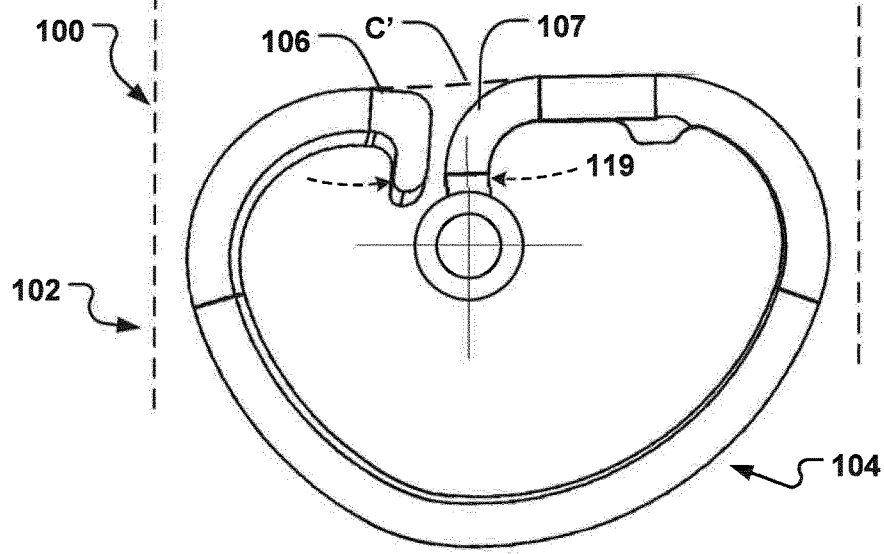
Figure 2:
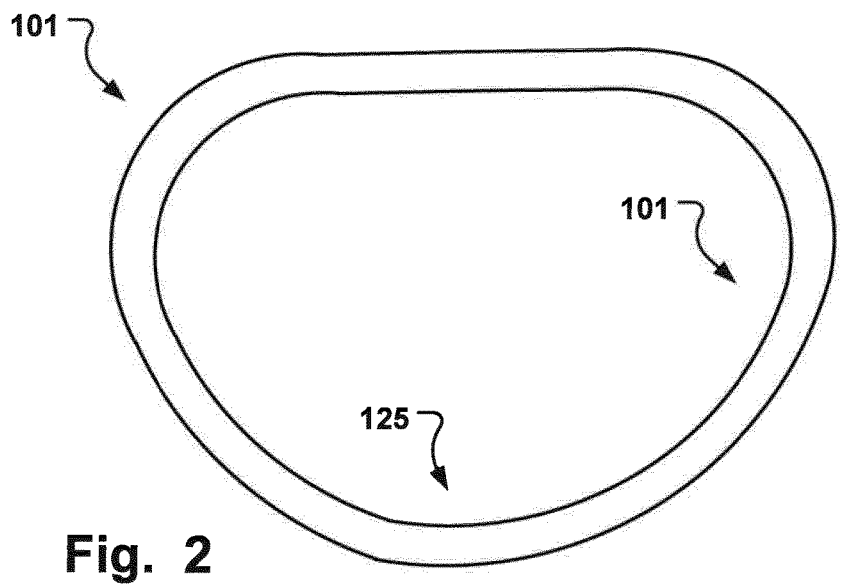
FIG. 2 is an illustration of a cardiac valve implant to be positioned with a medical device according to embodiments of the invention.
Figure 7:
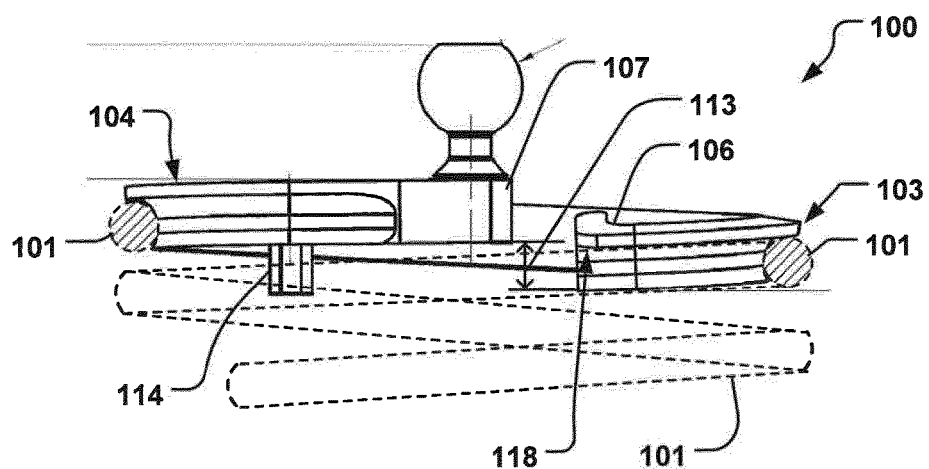
FIG. 7 is a side view of a medical device according to an embodiment of the invention when holding a cardiac valve implant according to FIG. 6 in place.

FIGS. 1a-b show a medical device 100 according to an embodiment of the invention, for holding an annuloplasty implant 101 (see e.g. FIG. 2 and FIG. 7). The device 100 comprises an elongate support 102 defining a peripheral edge 103 with a curvature about which the annuloplasty implant 101 can be fitted. The support 102 comprises a resilient portion 104 for resiliently holding the annuloplasty implant 101 in place in the medical device 100. The medical device 100 functions as a holder for the implant, and by having a resilient portion 104 the implant 101 can be held in place without the need for any specialized means for attachment, such as sutures and/or the use of holders with several components that are required to hold the implant. Easy attachment and detachment of the implant 101 to the device 101 is thereby achieved, in a less time-consuming manner compared to e.g. using sutures. As the implant 101 has been positioned at a target site, e.g. to resize the annulus of a heart valve, repositioning can be achieved readily by again attaching the implant to the device due to the resilient portion 104, again without the need of a special attachment means. Repeated repositioning is possible in this manner, during a narrow time frame during surgery, due to the quick attachment and detachment possible. The resilient portion 104 is for radially resiliently holding the implant 101 in place in the medical device 100, and/or axially resiliently holding the implant 101 in place in the medical device 100. Radially resiliently holding of the implant 101 is to be construed as the resilient portion 104 is resilient in the radial direction, which direction extends parallel to an axis from the center of the device 100 towards the peripheral edge 103, and thereby providing a force in the radial direction, either radially outwards from the center or radially inwards from the center, for holding the implant 101. The center of the device 100 may be construed as its center of mass, or geometrical center. The radial direction may also be construed as extending along an axis aligned from the position of the control member 110 to the peripheral edge 103. The implant 101 is held in place against the device 100 by the frictional force created in the contact area between the implant 101 and the device 100, e.g. at the peripheral edge 103, which source from the radially directed force applied through the resilient portion 104.

Figure 3:
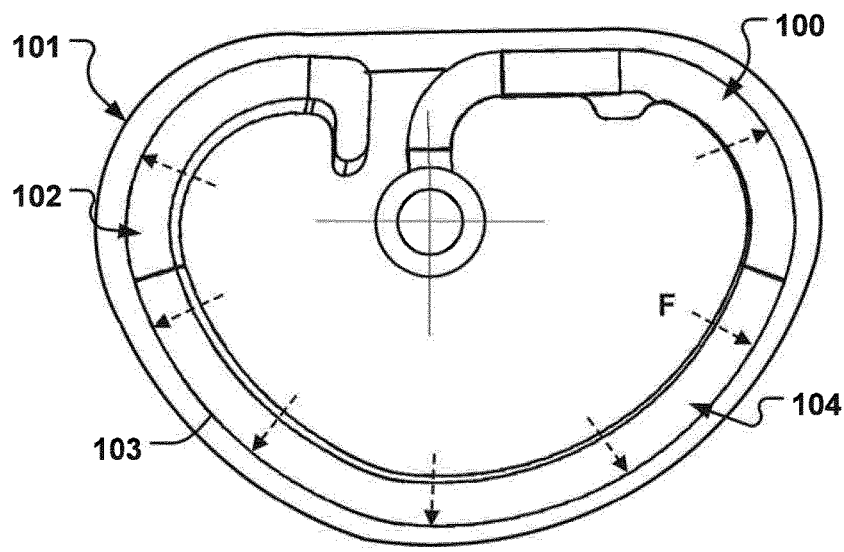
FIG. 3 is an illustration of a cardiac valve implant held in place for positioning with a medical device according to embodiments of the invention.

FIG. 2 shows an annuloplasty ring 101 as an example of an annuloplasty implant 101. In FIG. 3 the elongate support 102 is resilient itself and the resilient portion 104 extends therefore along the peripheral edge 103. The resilient portion 104 holds the implant 101 by applying the radial force (F) along the peripheral edge 103. The force (F) is here applied radially outwards.

Axially resiliently holding of the implant 101 is to be construed as the resilient portion 104 is resilient in the axial direction, which direction extends substantially perpendicular to the radial direction, i.e. the vertical direction in e.g. FIG. 7 showing a side view of the device 100 in FIGS. 1a-b. By being resilient in the axial direction the resilient portion 104 may exert a force in the axial direction onto the implant 101 that holds the implant 101 in place. As discussed further below with reference to FIG. 7 the geometry of the implant may in this manner be changed by the applied force from the resilient portion 104 for facilitating insertion of the implant.

Returning to FIGS. 1a-b, the support 104 has an expanded circumference (C) in a first configuration (FIG. 1a), and a reduced circumference (C') in a second configuration (FIG. 1b). The circumference is to be construed in its usual meaning, as the dimension of the device 100 around the peripheral edge 103. Where the elongate support is discontinuous, e.g. with two free ends as illustrated in FIGS. 1a-b, the circumference is measured as the shortest distance between the free ends at the periphery, as indicated by the dashed line (C, C'). Radial movement of the support 102 between the second and first configuration cause the curvature of the peripheral edge 103 to conform at least partly to the annuloplasty implant 101 to hold the annuloplasty implant 101 in place. The radial movement is due to the resilience of the resilient portion 104. Radial movement between the second and first configuration is to be construed as movement from second to first configuration, or movement from first to second configuration, i.e. radially outward and radially inward. The elongate support 102 may therefore apply a force to the implant 101 in both radially outward and radially inward directions to hold the implant in place. A self-holding action is thereby provided which allows easy removal of the implant from the device 100 and re-insertion if desired. By having an elongate support that is self-holding the disadvantageous prior art solutions with several components for holding the implant are avoided, and no sutures are needed.

The first configuration of expanded circumference (C) may be the relaxed configuration of the device 100, and the second configuration of reduced circumference may be the compressed configuration of the device 100. The resilient portion 104 is unloaded in the relaxed configuration and is loaded, i.e. being tensioned, in the compressed configuration. Hence, as was illustrated in FIG. 3, the radial movement is radial expansion from the second configuration to the first configuration, which causes the curvature of the peripheral edge 103 to conform to the implant 101 and exert a force (F) in the radially outward direction to hold the implant 101 in place. The configuration of the device 100 in FIG. 3 is therefore not the fully expanded circumference, i.e. not fully relaxed, in order to exert the force (F) on the implant 101. Thus, once the device 100 is put into place in the implant 101, it provides a firm support and the implant 101 and the device 100 can be manipulated without loosing the self-holding contact between the two. An elongate support with a circumference that merely can be changed is not sufficient to solve the aforementioned problems. Previous solutions still rely on having multiple component holder members that must be connected lock the implant in place, and to prevent collapsing of the holder members. The resilient portion 104 of the device 100 being radially expandable between to configurations, as discussed above, avoids such complex mounting systems.

In case of the device 100 apply a radially inward force to the implant (not shown), FIG. 1b illustrates the relaxed configuration, and the resilience of the portion 104 allows expansion of the device 100 to expanded circumference in FIG. 1a. The implant 101 may then conform to the inward edge of the device 100, opposite to peripheral edge 103 to hold it in place.

The resilience of the device 100 in embodiments may be due to the resilient portion 104 being made of a flexible material with shape memory properties, such as a shape memory polymer or metal. Alternatively, the device configurations of expanded and reduced circumference may be achieved by a material of the device 100 having other shape memory properties, such as temperature dependent shapes.

The elongate support 102 may be ring-shaped with at least one central opening 105. As seen in FIG. 1a, the central opening 105 has a substantial area due to the cross-section of the material of the elongate support 102 being substantially smaller than the diameter of the device 100 at any point. This improves the visibility of through the device 100, which is important during the implantation procedure.

In embodiments such as in FIG. 1a the ring-shape is discontinuous so that the elongate support 102 comprises two free ends 106, 107. The free ends 106, 107, allow movement in relation to each other, hence allowing the circumference of the device 100 to be varied to conform to the implant 101. The general shape of the elongate support 102 may be D-shaped, C-shaped, or shaped suitably to allow conforming to the implant 101 while permitting varying of the circumference. In case of not having a discontinuous ring-shape, i.e. a closed ring of any shape, the circumference may be reduced by pulling or compressing the resilient portion 104 inwards and towards the center of the device 100. The circumference of the device 100, which would be reduced by said pulling action, should in that case be construed as the shortest path around the periphery, i.e. a circular/oval path without following portions of the edges 103 being pulled towards the center, i.e. extending towards the center. Hence, this would effectively be the cross-section of the device 100, which would decrease by the pulling action. The device 100 may have struts crossing the opening 105 that are arranged so that compressing the struts towards each other the cross-section of the device 100 would be reduced.

As mentioned above, the entire elongate support 102 may be flexible to define the resilient portion 104. This may simplify manufacturing of the device 100, or provide a sufficiently uniform flexibility around the peripheral edge 103 to allow the entire elongate support 102 to conform to the implant 101, as illustrated in FIG. 3, thereby leaving no openings between the edge 103 and the implant 101 for secure attachment. Alternatively, a limited portion of the elongate support may be flexible, and/or the flexibility me be provided by other means such as a spring (not shown) arranged to join two parts of the elongate support 102 together, thereby allowing flexibility between the two parts for varying the circumference of the device 100.

Figure 10:
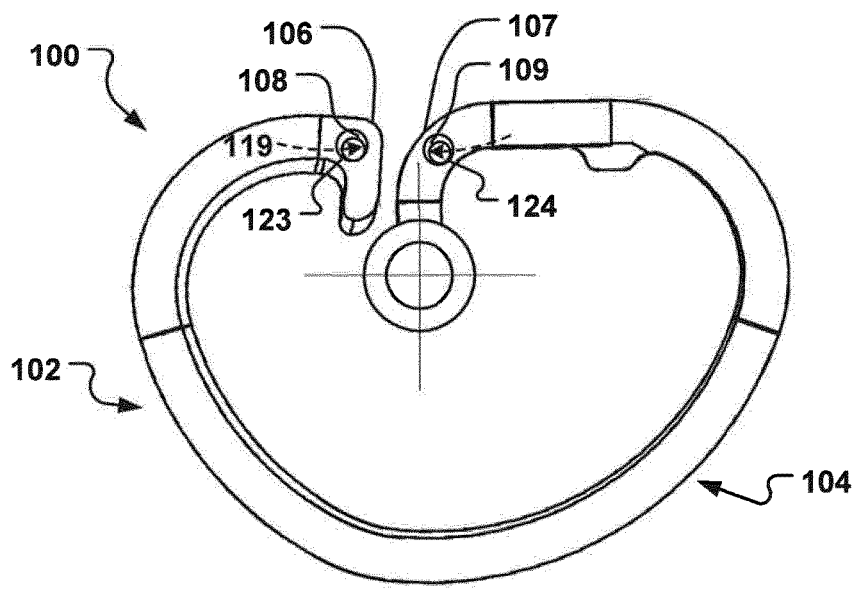
FIG. 10 is an illustration of a medical device according to an embodiment of the invention in a second configuration corresponding to FIG. 1b.

Each of the free ends 106, 107, may comprise an engagement portion 106, 107, having an engagement surface 108, 109, as illustrated in FIG. 1a. The engagement surfaces 108, 109, are adapted to receive a tool for compressing the free ends 106, 107, towards each other in the compressed configuration of the elongate support 102. The direction of compression is indicated for the free ends 106, 107, in FIG. 1b, and is for one end 107 indicated as a first direction 119, and being reversed for the opposite free end 106. Alternatively, if the configuration of reduced circumference (C') would be the relaxed shape, as elucidated above, the free ends may be forced apart by engaging with a tool 200 the surfaces opposite to that of the engagement surfaces 108, 109, for each of the free ends 106, 107. By having engagement surfaces 108, 109, the free ends 106, 107, may be manipulated to achieve the desired shape of the elongate support 102 to be able to conform to the cardiac valve implant 101 and hold it in place. This is an efficient and quick way of manipulating the device 100. Due to the free ends 106, 107, being manipulated directly a compact device 100 is realized. Visibility through the elongate support 102 is optimized due to manipulation at the periphery of the elongate support 102. Alternatively or in addition, the free ends 106, 107, may have openings 123, 124, with corresponding engagement surfaces 108, 109, for allowing insertion with a tool to manipulate the free ends 106, 107, as illustrated in FIG. 10. It may be advantageous to engage with the tool as close to the elongate support as possible, i.e. either by openings 123, 124, or by the control member 110, discussed further below, being displaced from the center of the support 102 and positioned close to the peripheral edge 103. Such positioning can improve the ability to position the implant 101 at the target site. Further, improved visibility through the implant 101 is obtained.

The engagement portion 106, 107, and the engagement surface 108, 109, may extend in a radial direction from the peripheral edge 103 of the elongate support 102. In FIGS. 1a-b the engagement surfaces 108, 109, extend radially inwards from the edge 103. A compact device 100 is thereby provided. Alternatively, the engagement surfaces 108, 109, may extend radially outwards from the edge 103. The spatial extent of the engagement surfaces 108, 109, may be optimized for allowing sufficient grip with a tool 200 while visibility is maintained by being confined largely to the periphery of the elongate support 102.

The device 100 may comprise a control member 110 for engagement with a positioning tool 200 as seen in FIGS. 11a-c. The control member 110 may comprise a spherical surface 117, as illustrated in the perspective view of the device 100 in FIG. 4. By having a spherical surface 117 the device 100 may pivot in a mating spherical recess 201 of the positioning tool 200. Such pivoting allows the device 100 to be rotated in any desired direction in relation to the positioning tool 200, see e.g. FIG. 11a, which for example allows insertion into the body in a minimally invasive manner, such as through the ribs of the body, and subsequent reorientation when being positioned for implantation at the target site.

The positioning tool 200 in FIGS. 11a-c may be used as a combination instrument. The distal end 202 of the tool 200 is arranged for manipulation of the free ends 106, 107, of the device 100, by contacting the engagement surfaces 108, 109. Also, the spherical recess 201 mates with the spherical surface 117 for pivotable positioning of the device 100. The spherical recess 201 is illustrated in FIG. 11c which is a magnification of the distal end 202 seen in FIGS. 11a, and 11b. In FIG. 11c the device 100 holding the implant 101 is pivotably held with the tool 200 via control member 110 having the spherical surface 117. Positioning of the device 100 onto the implant 101 and delivering of the implant 101 to the target site is thereby achieved with the same tool 200. Other types of tools having a spherical recess 201 and engagement members for the free ends 106, 107, and can be used with the device according to the above. Support tool 400, shown in FIGS. 13a-b, 14a-d, and described further below, also comprise the support itself by having two separated elongate support members attached to its distal end for allowing a wider range of movement of the support to conform to a wider range of implant sizes.

Figure 6:
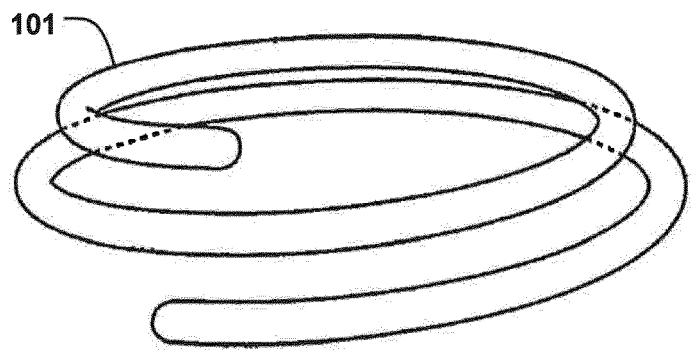
FIG. 6 is an illustration of a cardiac valve implant to be positioned with a medical device according to embodiments of the invention.

The control member 110 may be fixed to one of the free ends 106, 107, off-center from the central opening 105. In FIG. 1a, the control member 110 is fixed to the free end 107, and is positioned slightly above the center of the opening in vertical direction. This may provide increased visibility through the opening 105. At the same time the control member 110 may be positioned slightly towards the center, and alternatively at the center of the device 100, so that rotation of the device 100 around an axis extending through the control member 110, i.e. substantially perpendicular to the plane spanned by the curvature of the elongate support 102, corresponds to a rotation of the device 100 substantially around it central axis without lateral displacement. This may ease the positioning at the target site if the implant 101 is to be turned into position, as in the case of having a helical implant 101 as illustrated in FIG. 6. Further, the device 100 may be used to hold helical downsizing tools, such as disclosed in WO2009/080801.

In FIG. 1a the engagement portions 106, 107, extend radially inwards from the peripheral edge 103, and the control portion 110 is fixed to an end 111 of the engagement portion 107. By having the control member 110 fixed to an end of one of the engagement portions 106, 107, it is easy to switch mode from attaching or detaching the device 100 to/from the implant 101 by engaging the contact surfaces 108, 109, and to engaging the control member 110 for moving the device 100 to or from the target site. The switch can be made in one fluent motion, by using the combination tool 200, and reduces the time of the procedure and generally provides an increased degree of control. As mentioned above, the device 100 can be made compact in this manner, e.g. no additional fixation structures for the control member 110 extending across the opening 105 are necessary, improving visibility.

Figure 5A:
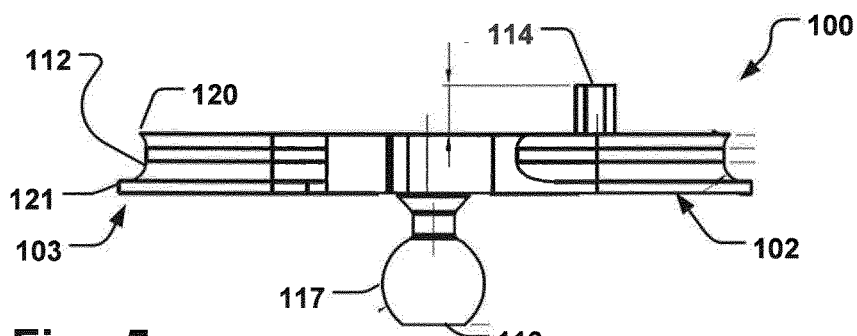
FIGS. 5a-b are side views of a medical device according to an embodiment of the invention, when not holding a cardiac valve implant (a), and when holding a cardiac valve implant in place (b)
Figure 5B:
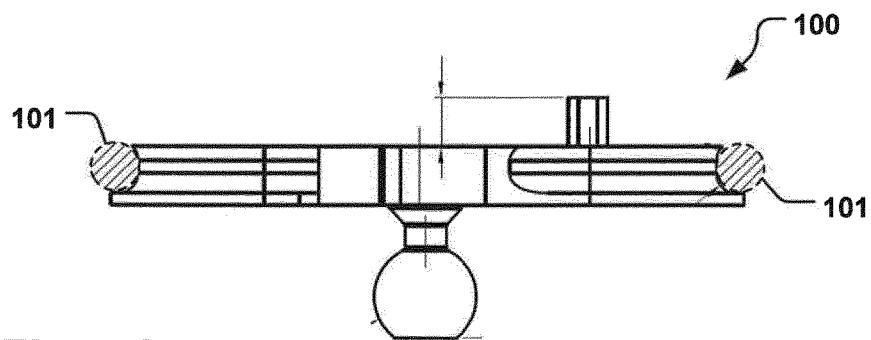

The elongate support 102 may comprise a radially outwardly opening or groove 112 along the peripheral edge 103 dimensioned to receive the annuloplasty implant 101. This is illustrated in FIGS. 5a-b which corresponds to side views of the device 100 in FIGS. 1a-b, with and without holding of the implant 101 in FIGS. 5a and 5b, respectively. The groove 112 provides efficient retaining of the implant 101 by the device 100. The groove 112 may have a curvature similar to that of the implant 101, so that the contact surface between the implant 101 and the device is increased, thereby allowing a further increased retaining force of the implant 101. Upon expansion of the elongate support 102 from the configuration of reduced circumference (C') to the configuration of increased circumference (C) the groove 112 conforms to the implant 101 as seen in FIG. 5b.

The recessed surface of the groove 112 may have other shapes to fit other types of implants, such as triangular, rectangular or oval. The groove 112 has side edges 120, 121, between which the recessed surface of the groove 112 extends. The side edges 120, 121, extend along the groove around the elongate support 102, and may be offset in relation to each other in the radial direction. I.e. in FIG. 5a the first side edge 120 extending on the side of the elongate support 102 opposite to that side of which the control member 110 extends from, i.e. the distal side, has a shorter radial extent than the second side edge 121. This may provide for an easier positioning of the implant 101 into the groove 112, as the circumference of the elongate support 102 at the location of the first side edge 120 at the distal side is smaller than that of the second side edge 121. Hence, less compression of the resilient member 104 of the elongate support 102 becomes necessary for the curvature to conform to the implant 101, when inserted from the distal side.

Figure 4:
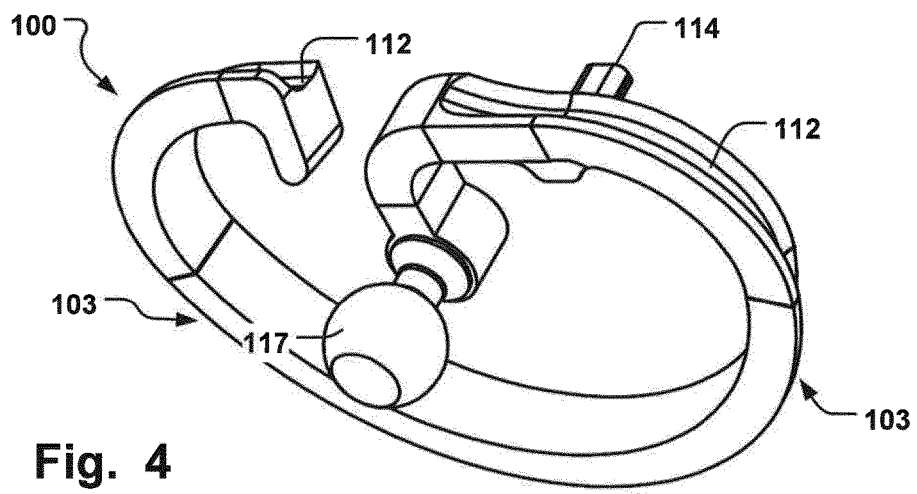
FIG. 4 is a perspective view of a medical device according to an embodiment of the invention.
Figure 9:
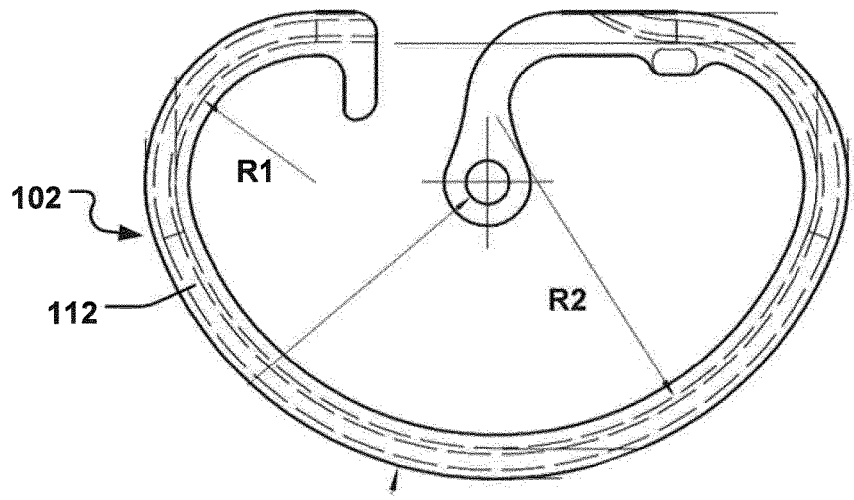
FIG. 9 is an illustration of a medical device according to an embodiment of the invention.

FIG. 4 shows a perspective view of the device 100. The groove 112 extends around the elongate member 102, which is shown in further detail in FIG. 9, which is a top down view, similar to that in FIGS. 1a-b, of the device 100. Also indicated in FIG. 9 is the different radius of curvature (R1, R2) of the elongate support 102. As mentioned above, the shape of the elongate support may vary, and the radius of curvature may vary along the elongate support 102.

The curvature of the peripheral edge 103 of the elongate support 102 may generally follow a three-dimensional path 118 such that the curvature conforms to an annuloplasty implant 101 extending in a corresponding three-dimensional path. Various implants 101 having different shapes can thereby be held in place by the device 100. An example is illustrated in FIG. 7, where the peripheral edge 103 follows the path 118 of the implant 101, seen in FIG. 6, which is marked by dashed lines. Here the discontinuous ring-shape of the elongate support 102 generally follows a three-dimensional path 118 such that the free ends 106, 107, are axially off-set 113. The off-set 113 is in the axial direction which is substantially perpendicular to the plane spanned by the elongate support 102 in the radial direction. The off-set 118 is such that the curvature of peripheral edge 103 follows the helix-shaped implant 101. The off-set 113 may be adjusted to fit the helix-shaped implant 101 if the distance between adjacent turns of the helix is varied. Alternatively the free ends 106, 107, way be aligned without off-set 113, but the peripheral edge 103 at other parts of the elongate member 102 may follow a curvature or path 118 in the axial direction, e.g. at a mid-section of the elongate support 102 between the free ends 106, 107. For example, implants 101 may have the posterior side 125, as indicated in FIG. 2, elevated in the axial direction from the other parts of the implant 101, and the elongate member 102 may be elevated at the corresponding portion to conform to the entire curvature of the implant 101. Other implants 101 may be saddle-shaped, i.e. convex or concave, or be asymmetrical in various configurations, whereby the elongate member 102 has the corresponding saddle shape or asymmetry.

The spatial extent of the path 118 may also provide for modifying the geometry of the implant 101. For example, the off-set 113 may be increased to force the rings of a helical implant 101, in FIG. 6, apart when the implant 101 is held in place by the device 100. This may facilitate insertion of the implant 100 through the annulus at the target site, as friction against the tissue may be reduced. When the device 100 is removed from the implant 101, the helical rings may assume their unstrained condition. By being resilient in the axial direction the resilient portion 104, which may be defined by the entire elongate support 102 being resilient, the geometry of the implant 101 may be modified by first compressing the device 100 in the axial direction and fit it to the implant 101, and then let the device 100 relax, whereby the implant 101, in this case being flexible, follows the expansion of the device 101. The groove 112 provides for locking the implant 101 in place and thereby forcing the rings of the implant 101 to follow the path 118 of the elongate support 102 when the elongate support 102 assumes its relaxed configuration.

The elongate support 102 may comprise a retainer pin 114 extending axially in a direction substantially perpendicular to a plane spanned by the curvature of the peripheral edge 103, as illustrated in FIGS. 4 and 5a. The retainer pin 114 is arranged to exert a radial force on the annuloplasty implant 101 to stop radial movement of the annuloplasty implant 101 when held in place by the device 100. The implant 101 is thereby prevented from slipping off the device 100, as radial movement is prevented by the pin 114. In particular, when the device 100 and the implant 101 is rotated, the force exerted on the implant 101 by surrounding tissue may cause a displacement in the radial direction, which now is prevented by the pin 14. A safer procedure and an improved grip of the implant is therefore achieved. As seen in FIG. 7, the retainer pin 114 extends from the distal side of the elongate support, i.e. in relation to the control member 110, and is placed such that it is in abutment with the implant 101, i.e. one of the helical rings of the implant 101. The position of the retainer pin 114 is seen also in the perspective view in FIG. 4, however it may be positioned at any part of the elongate support 102 provided it prevents radial movement of the implant 101.

Figure 8A:
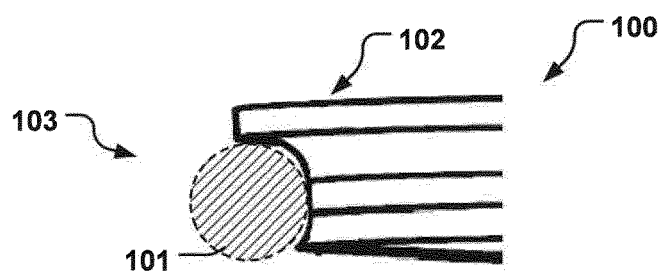
FIGS. 8a-c are side views of a detail a medical device according to embodiments of the invention when holding a cardiac valve implant in place.
Figure 8B:
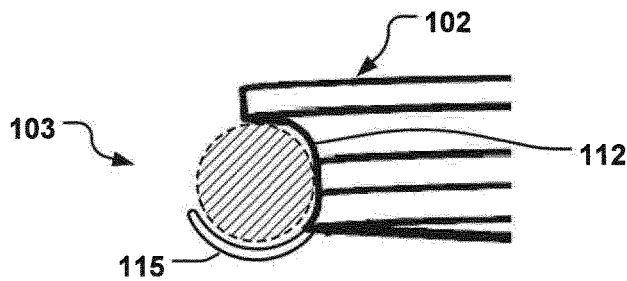

The elongate support 102 may comprise a friction reducing sheath 115 along the peripheral edge 103 which extends in a radial direction to cover a portion of the annuloplasty implant 101 when held in place by the device 100. By covering a part of the implant 101 when held in position by the sheath the friction is reduced between the implant 101 and the surrounding tissue. This allows the implant 101 to be more easily positioned without getting stuck on the tissue, for example when rotating the implant 101 into place at a target site such as through the leaflets of a valve. FIG. 8a shows a detail part of the elongate support 102 at the peripheral edge 103 with the implant held in place at the edge 103. FIG. 8b illustrates the friction reducing sheath 115 extending in the radial direction and covering a part of the implant 101. The sheath 115 may extend along the entire edge 103 of the elongate support 102. The sheath 115 will now prevent the tissue from contacting part of the implant 101. The amount of coverage of the implant 101 by the sheath 115 may be varied by increasing or decreasing the length of the sheath 115. More coverage may be suitable in some applications where low friction is particularly required. The sheath 115 may conform to the curvature of the cross-section of the implant 101, or may have other shapes to provide protection from tissue while allowing sufficient ease of insert of the device 100 to the implant 101. The sheath may be made of any material such as a polymer or a metal alloy providing low friction.

Figure 8C:
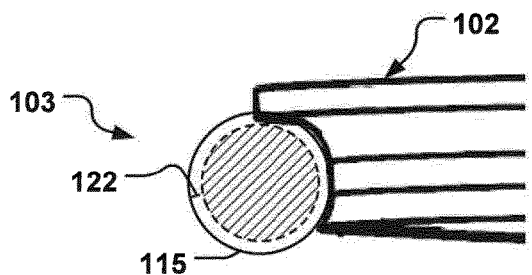

FIG. 8c shows an alternative configuration of the friction reducing sheath 115, covering the entire implant 101. The sheath 115 may be applied to the implant 101 before engaging with the device 100 and then, after being engaged and held in place by the device 100, removed when the implant 101 has been positioned at the target site. The sheath 115 may have an opening or discontinuity 122 which allows easy removal. In FIG. 8c, the sheath 115 may be fixated into the device 100 after the implant 101 is engaged with the edge 103, for example by a weld or glue portion between the sheath and the elongate member 102. When the implant 101 is inserted at the target site and the device 100 is removed, the sheath 115 will disengage from the implant 101 and be retracted together with the device 100. The opening or discontinuity 122 may allow for such disengagement.

The device 100 may comprise an indicator mark 116 being positioned at a first side of the elongate member 102 to mark a geometric feature of the implant 101 on a second opposite side of the elongate member 102, which may not be visible when the implant 101 is held in place at a target site. The allows easier maneuvering e.g. when an end of a helical implant 101, shown in FIG. 6, must be positioned at an opening of the annulus, but being obscured by the elongate support 102. Such indicator 116 is shown in FIG. 1a, and may be positioned anywhere on the device to facilitate the implantation procedure. Indicator marks may also be placed to mark anatomical features, such as the commissures. The indicator mark 116 may be made of a material visible in X-ray. The device 100 may have other indicators visible in X-ray or other imaging techniques, or the device 100 may be made in part or entirely of such material. The device 100 may have a channel or void containing a gas such as air as an indicator. Such indicators allow determination of the position and orientation of the device 100 in the body.

Figure 12:
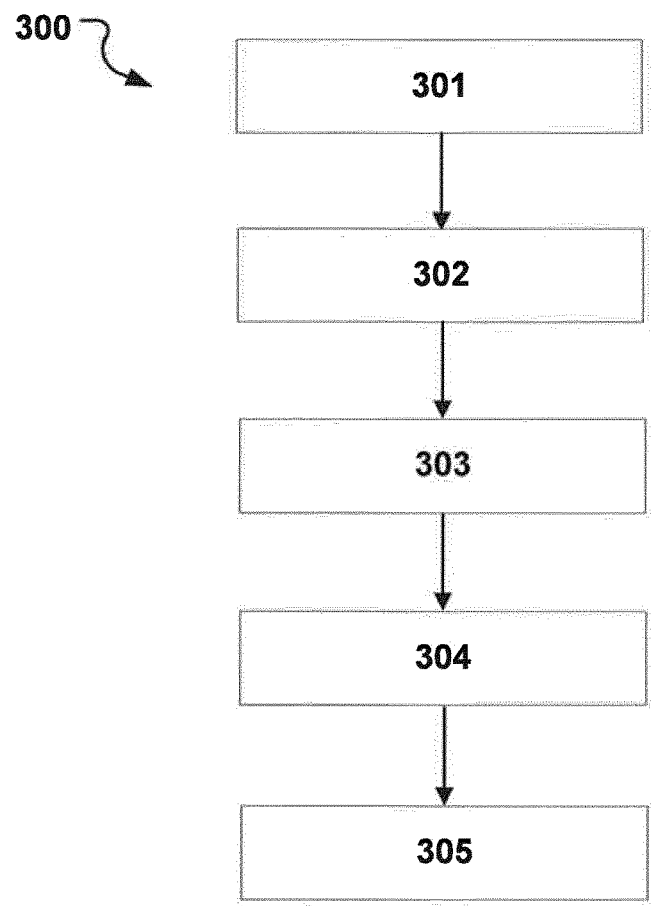
FIG. 12 is a flow chart illustrating a method of positioning a cardiac valve implant with a medical device according to embodiments of the invention.
Figure 15:
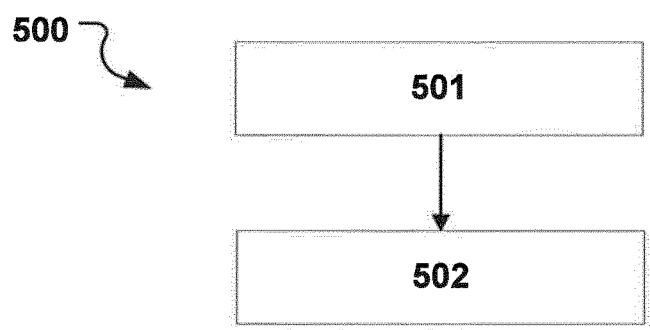
FIG. 15 is a flow chart illustrating a method of holding a cardiac valve implant (101) in place by a medical device.

FIG. 12 shows a flow diagram of a method 300 of positioning an annuloplasty implant 101 at a target site at an annulus with a medical device 100 having an elongate support 102 comprising a resilient portion 104. The method 300 comprises resiliently holding 301 the annuloplasty implant 101 in place in the device 100, positioning 303 the implant 101 at the target site, and loading 305 the resilient portion 104 for releasing the annuloplasty implant 101 from the device 100.

Resiliently holding the annuloplasty implant 101 may comprise loading 302 the resilient portion 104 for transforming the elongate support 102 from a first configuration to a second configuration, whereby radial movement of the elongate support 102 between the second and first configuration cause resiliently holding the annuloplasty implant 101 in place in the device 100.

Positioning the device 100 may comprise pivoting 304 the device 100 having a spherical surface 117 in a spherical recess 201 of a tool 200 for insertion into a body in a minimally invasive manner. The pivoting allows the device while held in place by the tool 200 to adapt to various anatomies to reach the target site. The pivoting 304 may comprise positioning the device 100 such that a plane spanned by the elongate support is substantially parallel to a longitudinal axis of the tool 200 for minimally invasive insertion. This is illustrated in FIG. 11a, where the device 100 is parallel to the longitudinal direction of the tool 200. This allows for example for insertion trough the ribs of a body.

Figure 13A:
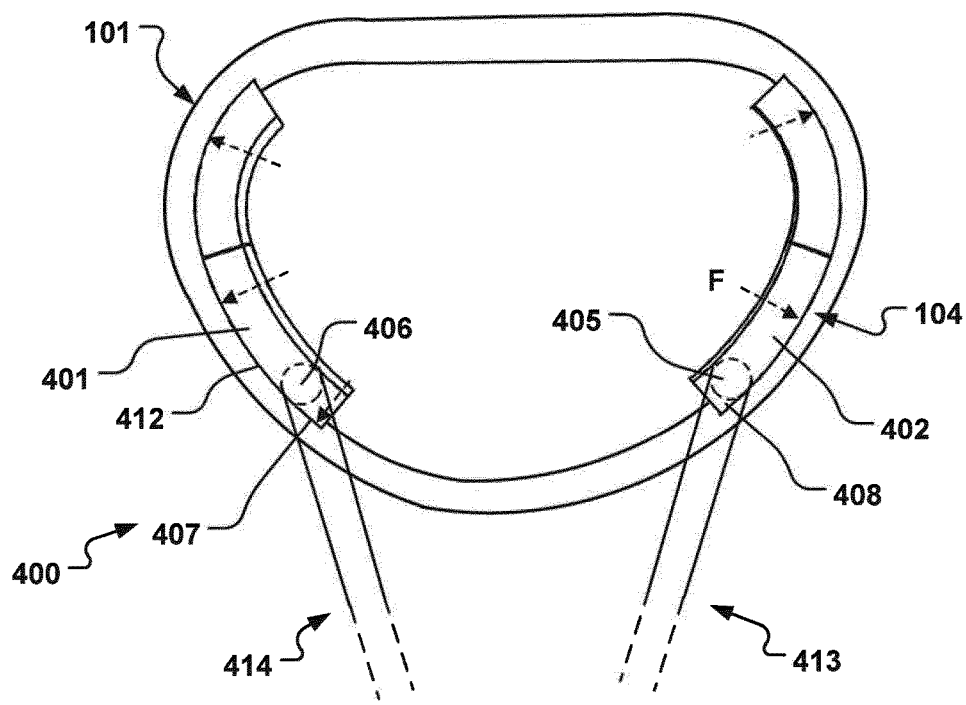
FIGS. 13a-b are illustrations of a support tool for holding a cardiac valve implant according to embodiments of the invention, in a top-down view (a) and from a side view (b), respectively.
Figure 13B:
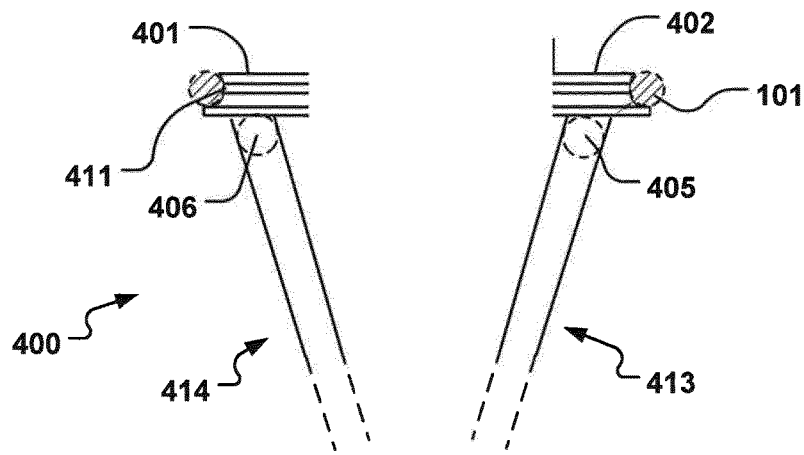

FIG. 13a shows a support tool 400 for holding a cardiac valve implant 101 comprising first and second elongate support members 401, 402, being separate and radially movable in relation to each other. FIG. 13a is a top-down view, and FIG. 13b is a corresponding side view of the illustration in FIG. 13a. Each of the support members 401, 402, has a curvature about which the cardiac valve implant 101 can be fitted. A manipulator portion 413, 414, is connected to the first and second support members 401, 402, for moving at least one of the first and second support members in relation to each other, to thereby cause the curvature to conform at least partly to the cardiac valve implant 101 and thereby to hold the cardiac valve implant in place. Because the support members 401, 402, are separate and movable in opposite radial directions the support tool 400 can be used to hold implants with a wide range of different sizes. There is no limitation in the support members 401, 402, for how wide or narrow they can be positioned, i.e. the manipulator portion 413, 414, such as a pair if pliers, or other types of manipulators such as illustrated in FIGS. 14a-d, can be adapted to allow movement in the whole range of sizes of possible implants 101. At the same time the curvature of the support members 401, 402, will provide a secure hold by conforming to the implant 101 to be held in place. The tool 400 is further advantageous if an implant needs to be removed once positioned at the target site for repositioning, e.g. the implant 101 can be rotated and manipulated with the secure hold of the supports 401, 402, without dislocating the implant 101.

Figures 14A, 14B, 14C:
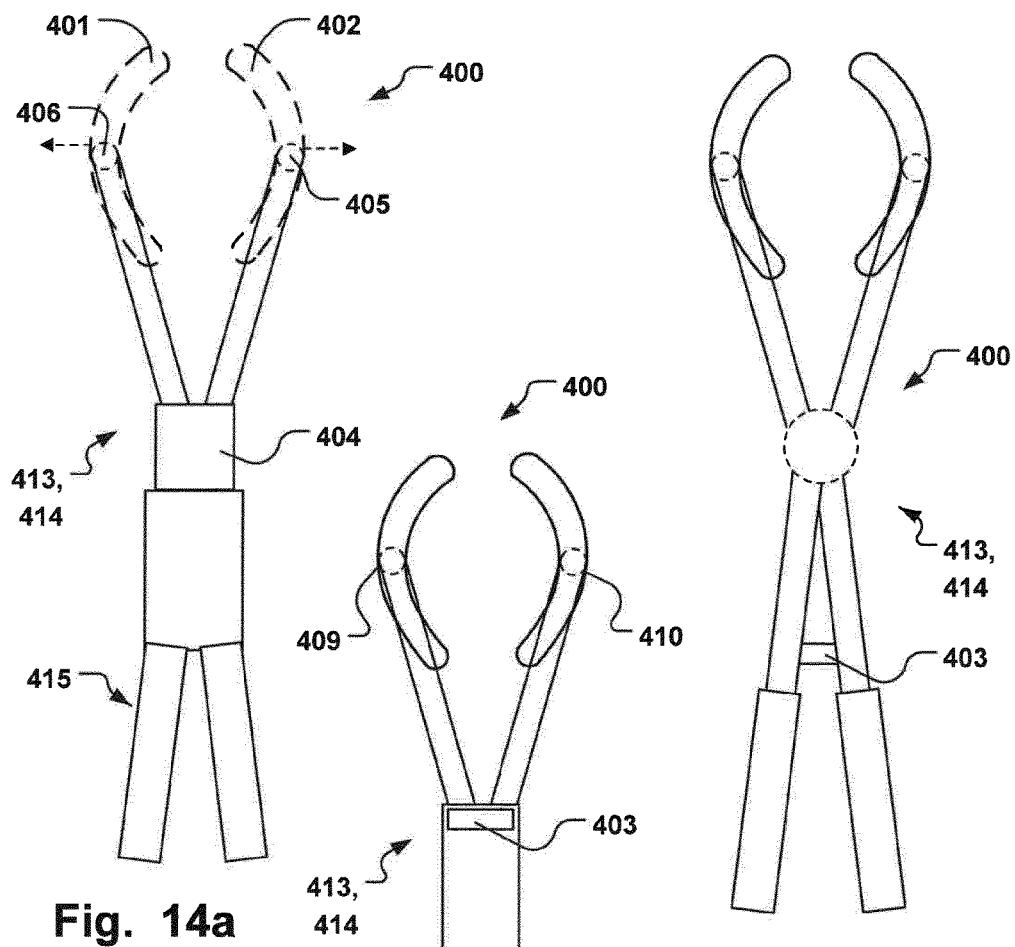
FIGS. 14a-d are further illustrations of a support tool for holding a cardiac valve implant according to embodiments of the invention.

The support tool 400 may comprise a biasing member 403, see e.g. FIG. 14c, for forcing the first and second elongate support members in an outward or inward radial direction when the manipulator portion 413, 414, move aforementioned support members 401, 402. Thereby a self-holding function is achieved. E.g. the biasing member may be a resilient portion 403, and for positioning the support tool 400 in the implant 101, the support members 401, 402, are urged towards each other by operating the manipulator portion 413, 414. A counter acting force exerted by the resilient portion 403 will subsequently provide expansion of the support members 401, 402, radially outwards against the implant 101 once the force inflicted by the movement of the manipulator portion 413, 414, is relaxed. The implant 101 may also be gripped from the outside with the force exerted by the biasing member 403 acting radially inwards towards the center of the implant 101.

The support tool 400 may comprise a locking portion 404 for locking the position of the first and second support members 401, 402, in relation to each other. This may be used in combination with the biasing member 403.

Figure 14D:
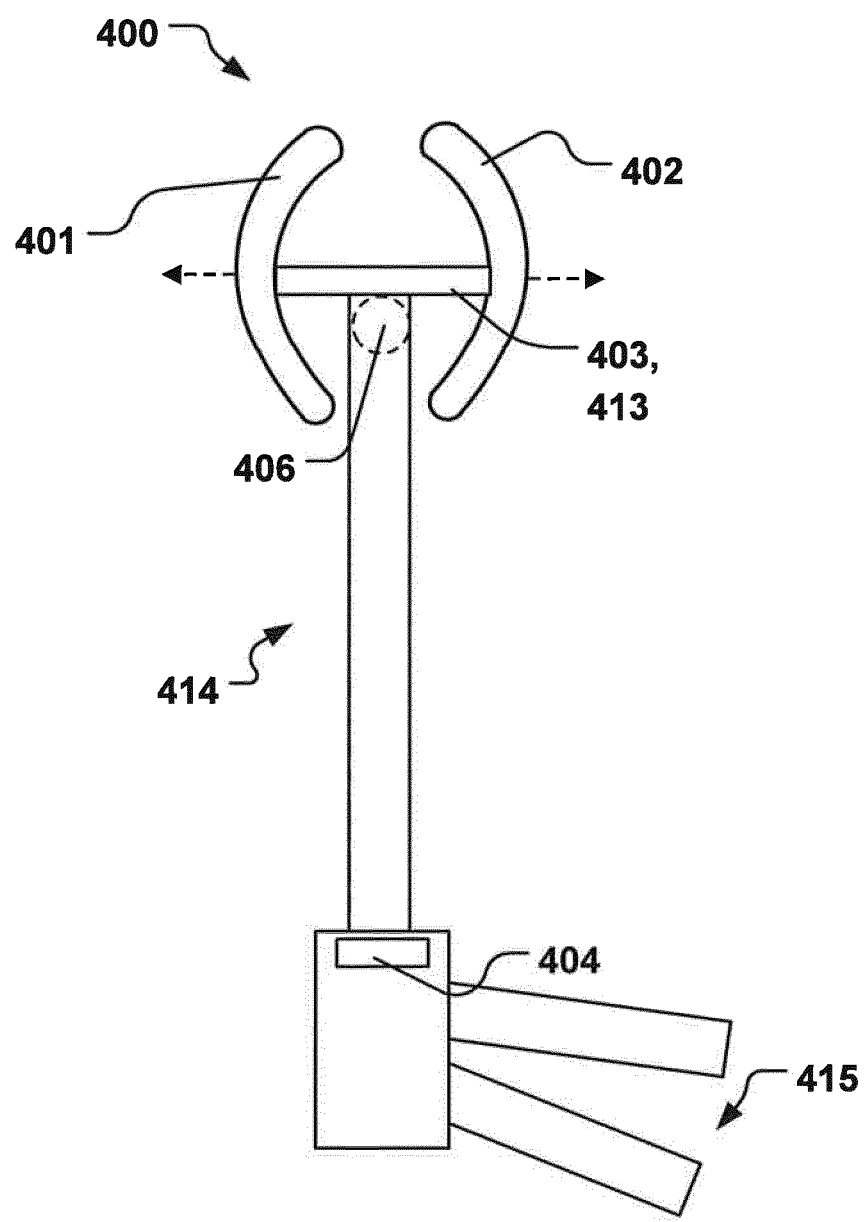

The support tool 400 may comprise at least one pivoting member 405, 406, for allowing pivoting motion between the manipulator portion 413, 414, and the first and second elongate support members 401, 402. The implant can thereby be held at various angles in relation to the manipulator tool 413, 414, for complying with different procedures and anatomies. There may be a single pivoting joint 406, as illustrated in FIG. 14d, that allows the support members 401, 402, to be pivoted simultaneously in the same plane. Alternatively or in addition the support tool 400 may comprise a first and second pivoting member 405, 406, between each of the first and second support members 401, 402, and the manipulator portion 413, 414, e.g. as illustrated in FIGS. 13a-b, and 14a-c. A wide range of customization is thus possible, where the left support 401 may have a different angle than the second support 402. A locking mechanism may be provided at the pivoting members 405, 406, for fixating the pivoting motion at an angle.

At least one of the first and second elongate support members 401, 402, may be resilient for allowing the curvature of the support members 401, 402, to be variable and to thereby conform to a range of varying size of cardiac valve implants. The support members 401, 402, may be resilient both in the radial direction, i.e. in the plane of the implant 101, or in the axial direction, i.e. perpendicular to the plane spanned by the implant 101, or a combination of both. A close and secure fit to any implant will thereby be provided as the peripheral edge 412 of the support member 401, 402, will conform along its entire curvature to the implant because of the resilient or flexible property. The support members 401, 402, may e.g. comprise a rubber material for allowing such resilience.

The first and second elongate support members 401, 402, are preferably radially movable in relation to each other for contacting substantially opposite sides of the implant 101. However, the members 401, 402, may be arranged to apposition the implant 101 at any relative angle to optimize the strength of the hold for implants of various shapes.

The manipulator portion 413, 414, may comprise pliers or forceps connected to the first and second elongate support members 401, 402, or any other device arranged for manipulating the relative position of the supports 401, 402, in the radial direction, as illustrated in FIGS. 14a-d. The drawings in FIGS. 13a-b, and 14a-d are not to scale, i.e. the distal portions of the devices 400 showing the elongate support members 401, 402, have been exaggerated in size for clarity of presentation. The manipulator 413, 414, may have appropriately arranged handles, or other means 415 for operating the manipulator for ease of use and safely operation.

FIG. 14d illustrates a support holder 400 that has a manipulating portion 413 combined with a biasing member 403 in a compact configuration arranged radially between the support members 401, 402, and a pivoting member 406 arranged substantially centrally between the supports 401, 402. The supports 401, 402, are moved radially outwards in the direction of the arrows by expansion of the manipulator portion 413 and/or the biasing member 403 to conform to the inside of the implant 101, and may be locked into position by locking portion 404, and/or have an outwardly acting bias force to hold the implant in place, that e.g. could be relieved by operating the handles 415 of the manipulator. The pivot angle between supports 401, 402, and manipulator portion 414 may be set via pivoting member 406.

Each of the first and second elongate support members 401, 402, may have a curvature corresponding to a circle sector of the implant 101, such as a commissural turn, or a posterior turn of the implant. It is therefore possible to adapt each of the supports 401, 402, to have a curvature that is suitable for the particular implant 101. E.g. the curvature of the first support 401 may correspond to a commissure turn, and the second support 402 may correspond to a posterior side. This enhances the conformity and provides a secure hold. The lengths of each of the support members 401, 402, may be varied, also independently from each other, to optimize a secure hold to the implant 101. The length of the support members 401, 402, may be such that they cover a substantial portion of the inner circumference of the implant 101. E.g. such as a ½, ⅓, or a ¼ of the inner circumference are in contact with the elongate support members 401, 402, for a secure hold. In combination with the conformation of the supports 401, 402, to the implant curvature this greatly enhances the grip compared to usual pliers or forceps.

The manipulator portion 413, 414, may be attached to the ends 407, 408, of the elongate support members 401, 402, in their longitudinal direction, respectively, as seen in FIG. 13a. Alternatively, the manipulator portion 413, 414, may be attached to the approximate centre points 409, 410, of the support members 401, 402, respectively, as seen in FIGS. 14a-d. The various configurations may be suitable for different procedures.

At least one of the first and second elongate support members may comprise a radially outwardly opening or groove 112, 411, along a peripheral edge 412 of the elongate support member 401, 402, which is dimensioned to receive the cardiac valve implant 101. This is illustrated in FIG. 13b. An improved secure hold to the implant 101 is thereby obtained.

As illustrated in FIG. 7, for the device 100, the support tool 400 may be configured such that at least one of the first and second elongate support members 401, 402, generally follows a three-dimensional path 118 such that ends 407, 408 of the support members 401, 402, are axially off-set 113. As described above, this allows a further improved secure hold to e.g. helix-shaped implants.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A medical device for holding a cardiac valve implant comprising an elongate support defining a peripheral edge with a curvature about which said cardiac valve implant can be fitted, wherein said elongate support comprises a resilient portion for resiliently holding said cardiac valve implant in place in said device, wherein said elongate support has an expanded circumference in a first configuration, and a reduced circumference in a second configuration, wherein radial movement of said elongate support between said second and first configuration cause said curvature to conform at least partly to said cardiac valve implant to hold said cardiac valve implant in place, and wherein said first configuration is relaxed and said second configuration is compressed, and said radial movement is radial expansion from said second configuration to said first configuration, and wherein said elongate support is ring-shaped, and wherein said ring-shape is discontinuous so that said elongate support comprises a first free end and a second free end, wherein a radially inner surface of said discontinuous ring-shape is continuous between the first free end and the second free end, and wherein said discontinuous ring-shape forms a three-dimensional path such that the first free end and the second free end are axially off-set in an axial direction, wherein the resilient portion is resilient in the axial direction, wherein, of the first free end and the second free end, only the first free end includes a control member extending in the axial direction relative to a plane spanning across the ring shape of the elongate support; and the control member comprising a spherical surface for pivotable engagement with a positioning tool, wherein the positioning tool is removably engaged with the control member.

2. Medical device according to claim 1, wherein said elongate support is flexible to define said resilient portion.

3. Medical device according to claim 1, wherein each of said first and second free ends comprises an engagement portion having an engagement surface adapted to receive a tool for compressing said first and second free ends towards each other in said compressed second configuration.

4. Medical device according to claim 3, wherein said engagement portion and said engagement surface extend in a radial direction from said peripheral edge of said elongate support.

5. Medical device according to claim 3, wherein said engagement portions extend radially inwards from said peripheral edge, and said control member is fixed to said engagement portion of the first free end.

6. Medical device according to claim 1, wherein said elongate support comprises a radially outwardly opening or groove along said peripheral edge dimensioned to receive said cardiac valve implant.

7. Medical device according to claim 1, wherein said elongate support comprises a retainer pin extending axially in a direction substantially perpendicular to a plane spanned by said curvature and arranged to exert a radial force on said cardiac valve implant to stop radial movement of said cardiac valve implant in use.

8. Medical device according to claim 1, wherein said elongate support comprises a friction reducing sheath along said peripheral edge and extending in a radial direction to cover a portion of said cardiac valve implant when held in place by said device.

9. Medical device according to claim 1, wherein said medical device comprises an indicator being positioned at a first side of said elongate member to mark a geometric feature of said cardiac valve implant on a second opposite side of said elongate member not being visible when, in use, said cardiac valve implant is held in place.

10. A kit comprising the medical device according to claim 1 and said positioning tool comprising a distal end arranged for manipulation of said resilient portion for resiliently holding a cardiac valve implant in place in said device.

11. Kit according to claim 10, wherein said distal end comprises a spherical recess for mating with the spherical surface of the control member of said medical device.

* * * * *